United States Patent [19]

Richardson et al.

[11] Patent Number: 4,503,063
[45] Date of Patent: Mar. 5, 1985

[54] N-ACYL 3-ARYL-3-HYDROXY-4-(1H-1,2,4-TRIAZOL-1-YL)-BUTYRAMIDE ANTIFUNGAL AGENTS

[75] Inventors: Kenneth Richardson, Canterbury; Kelvin Cooper, Ramsgate, both of England

[73] Assignee: Pfizer Inc., New York, N.Y.

[21] Appl. No.: 535,971

[22] Filed: Sep. 26, 1983

[30] Foreign Application Priority Data

May 7, 1983 [GB] United Kingdom ............... 8312624

[51] Int. Cl.³ .................. A01N 43/64; A61K 31/41; C07D 249/08; C07D 401/06
[52] U.S. Cl. .................. 514/383; 546/276; 548/259; 548/262; 514/340
[58] Field of Search ............. 548/262; 546/276; 424/263; 426/269

[56] References Cited

U.S. PATENT DOCUMENTS 4,394,151 7/1983 de Fraine et al. .............. 71/76

FOREIGN PATENT DOCUMENTS 0054974 6/1982 European Pat. Off. .......... 548/341
0055833 7/1982 European Pat. Off. .......... 548/262
0069448 1/1983 European Pat. Off. .......... 548/262
2104065 3/1983 United Kingdom ............ 548/262

Primary Examiner—Alton D. Rollins
Attorney, Agent, or Firm—Charles J. Knuth; Albert E. Frost; Paul D. Thomas

[57] ABSTRACT

Compounds of the formula

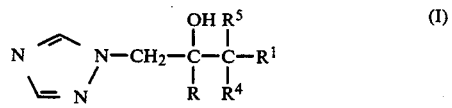

a pharmaceutically or agriculturally acceptable salt thereof, wherein R is 5-chloro-2-pyridyl or phenyl optionally substituted by one to three substituents, each independently selected from F, Cl, Br, I, $CF_3$, $C_1$–$C_4$ alkyl and $C_1$–$C_4$ alkoxy; $R^1$ is $CONR^2R^3$ where either
(a) $R^2$ is H or $C_1$–$C_4$ alkyl and $R^3$ is $C_2$–$C_4$ alkanoyl or optionally substituted benzoyl; or
(b) $R^2$ and $R^3$ are each ($C_1$–$C_4$ alkoxy)carbonyl; and $R^4$ and $R^5$ are each H or $CH_3$; methods for their use in combating fungal infections in plants, seeds and animals, including humans, and pharmaceutical and agricultural compositions containing them.

16 Claims, No Drawings

N-ACYL 3-ARYL-3-HYDROXY-4-(1H-1,2,4-TRIAZOL-1-YL)-BUTYRAMIDE ANTIFUNGAL AGENTS

BACKGROUND OF THE INVENTION

This invention relates to novel triazole derivatives which have antifungal activity and are useful in the treatment of fungal infections in animals, including humans, and as agricultural fungicides.

Published United Kingdom Patent Application GB No. 2,104,065A discloses compounds of the formula

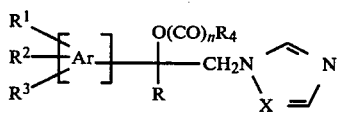

where, inter alia, X is N, n is 0, Ar is phenyl, $R_1$, $R_2$ and $R_3$ are each H, halogen, $C_1$-$C_3$ alkyl or $C_1$-$C_3$ alkoxy; $R_4$ is H, and R is $COOR_5$, $COSR_6$, $CONR_7R_8$ or CN; and $R_7$ and $R_8$ are each H, $C_1$-$C_6$ alkyl, $C_3$-$C_7$ cycloalkyl, phenyl or benzyl. The compounds are disclosed as useful in combating or preventing infestations of plants by microorganisms. There is no disclosure of human utility for these compounds.

U.S. Pat. No. 4,394,151 issued July 19, 1983 relates to fungicides and plant growth regulators of the general formula

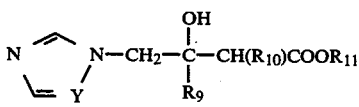

where, inter alia, Y is N, $R_9$ is optionally substituted phenyl, $R_{10}$ is H or alkyl and $R_{11}$ is H, alkyl, cycloalkyl, optionally substituted phenyl or optionally substituted benzyl or $R_9$ and $R_{10}$ taken together form a lactone. Here again, no disclosure of human utility is set forth.

European Patent Application No. 69,448 discloses compounds of the formula

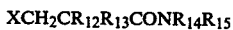

$$XCH_2CR_{12}R_{13}CONR_{14}R_{15}$$

where, inter alia, X is triazolyl, $R_{12}$ and $R_{13}$ are each optionally substituted phenyl provided that at least one of $R_{12}$ and $R_{13}$ contains at least one substituent; $R_{14}$ and $R_{15}$ are each H, alkyl, cycloalkyl, alkoxyalkyl, hydroxyalkyl, aminoalkyl, carboxyalkyl, phenyl or benzyl or, taken together with the nitrogen atom to which they are attached, they form a pyrrolidinyl, morpholino or a 4-substituted piperazino group. They are stated to be useful in treatment of fungal infections in plants, seeds and animals including humans.

European Patent Application No. 54974 discloses imidazole derivatives of the formula

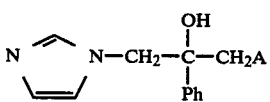

where Ph is phenyl optionally substituted with halogen and A is e.g., $NR_{16}R_{17}$ where $R_{16}$ and $R_{17}$ are each H, alkyl, cycloalkyl, or taken together with the adjacent nitrogen atom they form certain rings. They are stated to be useful as antifungal agents for humans.

SUMMARY OF THE INVENTION

According to the invention, there are provided compounds of the formula

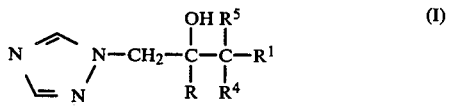

where R is phenyl optionally substituted by 1 to 3 substituents each independently selected from F, Cl, Br, I, $CF_3$, $C_1$-$C_4$ alkyl and $C_1$-$C_4$ alkoxy, or R is a 5-chloropyrid-2-yl group; $R^1$ is —$CONR^2R^3$ where either (a) $R^2$ is H or $C_1$-$C_4$ alkyl and $R^3$ is $C_2$-$C_4$-alkanoyl, benzoyl, benzoyl substituted by one or two substituents each independently selected from F, Cl, Br, I, $CF_3$, $C_1$-$C_4$ alkyl and $C_1$-$C_4$ alkoxy; or (b) $R^2$ and $R^3$ are both ($C_1$-$C_4$ alkoxy)carbonyl; $R^4$ and $R^5$ are each H or $CH_3$; and their pharmaceutically and agriculturally acceptable salts, especially acid addition salts.

The invention also provides a pharmaceutical composition comprising an antifungal amount of a compound of the formula (I) or pharmaceutically acceptable acid addition salt thereof, together with a pharmaceutically acceptable diluent or carrier.

The invention further provides a compound of the formula (I) or pharmaceutically acceptable acid addition salt thereof, for use in treating fungal infections in animals, including humans.

The invention also includes an agricultural composition suitable for use on a plant or seed comprising an antifungal amount of a compound of formula (I) or agriculturally acceptable acid addition salt thereof, together with an agriculturally acceptable diluent or carrier.

Yet further, the invention provides a method of treating an animal, including a human being, having a fungal infection, which comprises administering to the animal an antifungal effective amount of a compound of the formula (I) or pharmaceutically acceptable acid addition salt thereof.

The invention also includes a method of treating a seed or plant having a fungal infection, which comprises administering to the plant or seed, or to the locus of said plant, an antifungally effective amount of a compound of the formula (I) or of an agriculturally acceptable acid addition salt thereof.

When R is said phenyl group it is preferably phenyl substituted by 1 to 3 substituents, more preferably 1 or 2 substituents, each independently selected from F, Cl, Br, I and $CF_3$. Particularly preferred values of R include 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2,5-difluorophenyl, 2-fluoro-4-chlorophenyl, 2-chloro-4-fluorophenyl, 2,4,6-trifluorophenyl and 4-bromo-2,5-difluorophenyl.

Even more preferably R is 2,4-dichlorophenyl, 4-chlorophenyl or 2,4-difluorophenyl.

R is most preferably 2,4-dichlorophenyl or 2,4-difluorophenyl.

Particularly preferred as $R^1$ is $CONR^2R^3$ where either (a) $R^2$ is H and $R^3$ is acetyl, propionyl or p-chlorobenzoyl; or (b) $R^2$ and $R^3$ are both —COOCH$_3$.

$R^4$ and $R^5$ are each preferably H.

Where the compounds of formula (I) contain at least one chiral center, the invention includes both the resolved and unresolved forms.

DETAILED DESCRIPTION OF THE INVENTION

The compounds of the formula (I) in which $R^2$ is H or $C_1$–$C_4$ alkyl and $R^3$ is $C_2$–$C_4$ alkanoyl or said optionally substituted benzoyl group are prepared, for example, by reaction a compound of the formula $$\underset{N}{\overset{N}{\diagdown}}\hspace{-2pt}\diagup\hspace{-2pt} N-CH_2-\underset{R}{\overset{OH}{\underset{|}{C}}}-\underset{R^4}{\overset{R^5}{\underset{|}{C}}}-CONHR^2 \quad (II)$$

where $R^2$ is H or $C_1$–$C_4$ alkyl and R, $R^4$ and $R^5$ are as defined for formula (I), with either an acid halide or an acid anhydride of the formula $$R^3X \text{ or } (R^3)_2O$$

where $R^3$ is $C_2$–$C_4$ alkanoyl or said optionally substituted benzoyl group and X is Cl or Br.

When an acid halide is used, the reaction is desirably carried out in the presence of a base such as pyridine or sodium hydride.

The reaction is typically carried out in a suitable organic solvent, e.g., acetonitrile or tetrahydrofuran. It is not generally necessary to accelerate the reaction by heating, and the product can be isolated and purified conventionally.

The compounds of formula (I) in which $R^2$ and $R^3$ are both ($C_1$–$C_4$ alkoxy)carbonyl are prepared, for example, by reacting a compound of the formula (II) where $R^2$ is H with at least two equivalents of an alkyl haloformate of the formula $$X-\underset{O}{\overset{O}{\underset{\|}{C}}}-O-(C_1\text{–}C_4 \text{ alkyl})$$

where X is Cl or Br.

The reaction is carried out in a similar manner to that described above. Again the presence of a base is desirable.

The requisite starting materials for production of the invention compounds are prepared, for example, by one of the following methods.

(1) The starting amides of formula (II) wherein $R^2$, $R^4$ and $R^5$ are each hydrogen are prepared by the following reaction sequence $$\underset{N}{\overset{N}{\diagdown}}\hspace{-2pt}\diagup\hspace{-2pt} N-CH_2-\underset{R}{\overset{OH}{\underset{|}{C}}}-CH_2CN \xrightarrow[\text{dry HCl}]{C_1\text{–}C_4 \text{ alkanol}} \quad (III)$$

-continued $$\underset{N}{\overset{N}{\diagdown}}\hspace{-2pt}\diagup\hspace{-2pt} N-CH_2-\underset{R}{\overset{OH}{\underset{|}{C}}}-CH_2-C\underset{\text{.HCl}}{\overset{NH}{\diagdown \text{Oalkyl}}}$$

$$\downarrow H^\oplus/\text{Heat}$$

$$(II, R^2 = H)$$

The imido ether dihydrochloride is provided by reaction of the nitrile precursor of formula (III) in lower alkanol (preferably methanol or ethanol) saturated with anhydrous hydrogen chloride. The reaction is ordinarily carried out at room temperature or below. When the reaction is complete, the precipitated salt is collected and dried by conventional methods. The conversion of the imido ether salt to amide is ordinarily carried out by heating the reactants for a short period, preferably under reflux in a suitable high-boiling organic solvent such as 1,2-dichlorobenzene (b.p. 178°); the reaction is usually complete in about 15 minutes.

(2) Starting compounds of formula (II) in which $R^2$ is $C_1$–$C_4$ alkyl are prepared, for example, by the alkylation of the corresponding starting materials in which $R^2$ is H. The alkylation is typically carried out by dissolving the starting unsubstituted amide in a suitable organic solvent, e.g., dry tetrahydrofuran, followed by cooling to 0°–5° C. A strong base such as sodium hydride is then added. After stirring for a few minutes, an appropriate quantity of alkylating agent is added. The preferred alkylating agents are the alkali metal iodides and bromides. For monoalkylation, only one equivalent of alkylating agent is employed. The alkylated product are isolated from the reaction mixture by conventional techniques.

(3) Compound (II) in which $R^2$ is H or alkyl as defined above are also prepared as follows $$\underset{N}{\overset{N}{\diagdown}}\hspace{-2pt}\diagup\hspace{-2pt} N-CH_2-\underset{R}{\overset{OH}{\underset{|}{C}}}-\underset{R^4}{\overset{R^5}{\underset{|}{C}}}-CO_2H \xrightarrow{R^2NH_2} (II) \quad (IV)$$

Compound (IV) is preferably used in the form of its "functional equivalent as an acylating agent", e.g., as an acid chloride or bromide or a mixed anhydride or as a $C_1$–$C_4$ alkyl, succinimido, phthalimido or benzotriazol-1-yl ester.

All these "functional equivalents" are prepared conventionally from the acid (IV). The acid chlorides and bromides are, for example, prepared by reaction of said acid of formula (IV) with thionyl chloride or bromide, the mixed anhydrides by reaction with a $C_2$–$C_5$ alkanoyl chloride, the $C_1$–$C_4$ alkyl esters by simple esterification, and the succinimido, phthalimido and benzotriazol-1-yl esters by reaction with N-hydroxysuccinimide, N-hydroxyphthalimide or 1-hydroxybenzotriazole in the presence of a dehydrating agent such as dicyclohexylcarbodiimide.

In fact, it is preferred to use the compounds (IV) in the form of their succinimido esters of the formula

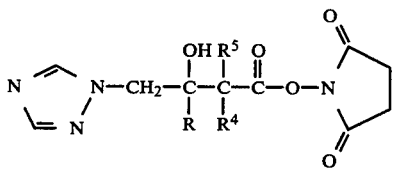

Thus in a typical procedure, dicyclohexylcarbodiimide dissolved in e.g., dry dioxan is added to a solution of the acid (IV) and N-hydroxysuccinimide in e.g., dry dioxan. After stirring for a few hours at room temperature and filtering, the reaction is generally completed by stirring the solution of the compound (V) with the amine $R^2NH_2$ at room temperature for a few hours in e.g., dry dioxan, after which the product is isolated and purified by conventional means.

If compound (IV) is reacted in its free acid form, the reaction should generally be carried out in the presence of a dehydrating agent such as dicyclohexylcarbodiimide.

The $C_1$-$C_4$ alkyl ester starting materials are, e.g., prepared as follows

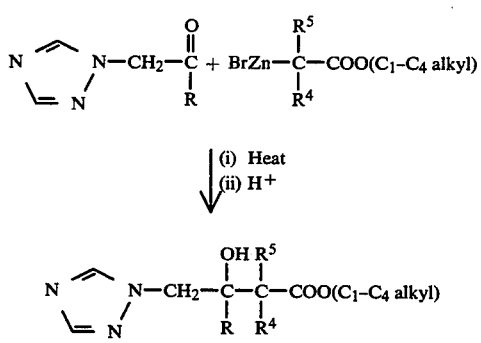

Generally some of the product (VI) cyclizes in situ under the reaction conditions to give the intermediate lactone (A). Mixtures of ester (VI) and lactone (A) are separated, e.g., by column chromatography.

The benzotriazol-1-yl esters have the formula

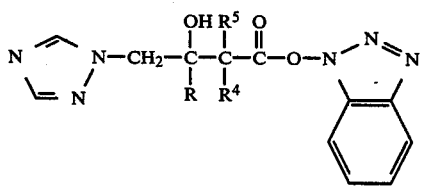

These are prepared as discussed above.

Thus in a typical procedure, dicyclohexylcarbodiimide, 1-hydroxybenzotriazole and the acid (IV) are stirred together at room temperature for a short period in e.g., dry dioxan. The reaction is generally completed by stirring the resulting intermediate (VII) with the amine $R^2NH_2$ at room temperature until the reaction is complete, after which the product is isolated and purified by conventional means.

(4) Compounds of the formula (II) in which $R^2$ is H are also prepared by the controlled hydrolysis of the corresponding nitriles. Typically this hydrolysis is carried out by heating the starting nitrile at about 70°-100° C., preferably 90°-95° C., with aqueous sulphuric acid, preferably 80%, by weight, until the formation of the amide is complete as monitored by thin-layer chromatography. Further hydrolysis to convert —$CONH_2$ to —COOH can be carried out under similar conditions, if desired.

(5) Starting amides of formula (II) where $R^2$ is as previously defined are also prepared from the intermediates of the formula (A) as follows

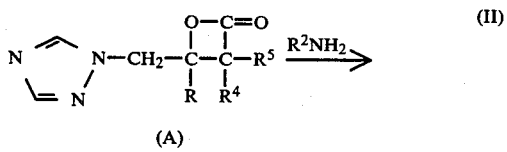

where R, $R^4$ and $R^5$ are as defined for formula (I), and $R^2$ is H or $C_1$-$C_4$ alkyl.

The reaction is carried out by stirring the reactants together in a suitable solvent, e.g., ethanol, at room temperature until the reaction is complete. If necessary, the reaction mixture is heated to accelerate the reaction. The product is then isolated and purified conventionally.

(6) An alternative method for preparation of certain starting amides of formula (II) where $R^2$, $R^4$ and $R^5$ are each H, is outlined below.

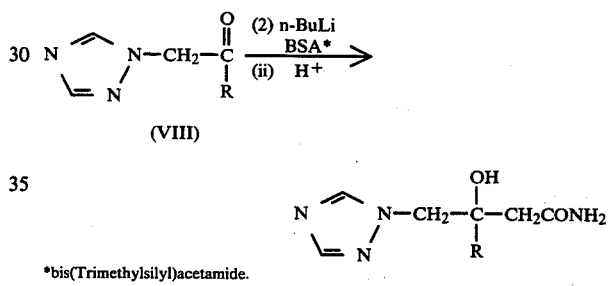

*bis(Trimethylsilyl)acetamide.

The reaction is typically carried out by stirring bis(trimethylsilyl)acetamide at −70° C. in dry tetrahydrofuran (THF) while n-butyllithium is added dropwise. The resulting solution is stirred at about −70° for a short period, then the ketone (VIII) in e.g., dry THF is slowly added, and the resulting mixture stirred at about −70° C. for a few hours. The reaction mixture is then allowed to warm to room temperature and aqueous acid is added, after which the product is isolated and purified conventionally.

(7) The lactone intermediates of the formula (A) are prepared by cyclization, preferably from an ester (IX) as illustrated below.

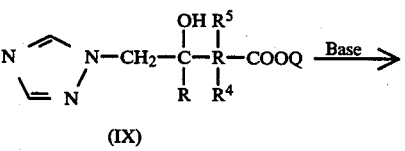

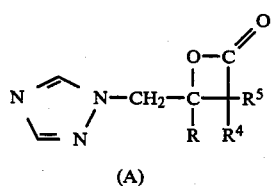

where Q=$C_1$-$C_4$ alkyl, phthalimido, succinimido or 1-benzotriazolyl.

The esters of formula (IX) are prepared as previously described. The cyclization is preferably carried out in the presence of a suitable base by stirring at room temperature. Preferred bases are tertiary amine bases, e.g., triethylamine and alkali metal hydrides, e.g., sodium hydride.

(8) The starting nitriles of formula (III) are provided, for example, by the following general method.

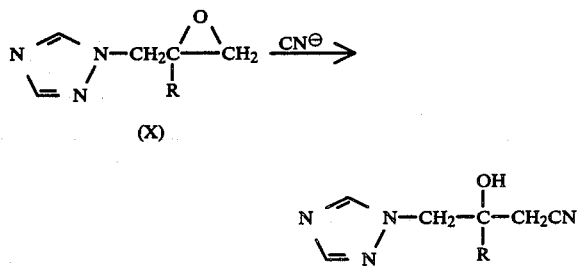

The preferred source of cyanide ions are the alkali metal cyanides, particularly sodium and potassium cyanide. In a typical procedure, the compound (X) and sodium or potassium cyanide are heated together in a suitable organic solvent, e.g., dimethylformamide, at up to 100° C., preferably 65°-70° C., for up to 6 hours. It is preferred to add the cyanide dropwise to the solution of the oxirane over, about a half hour. After cooling the reaction mixture and pouring it into water, the desired product is isolated and purified by conventional techniques.

The starting materials of the formula (X) are in many cases known compounds (see e.g., European Patent Application Publication No. 44605) or can be prepared by routine methods as will be known to those skilled in the art, for example,

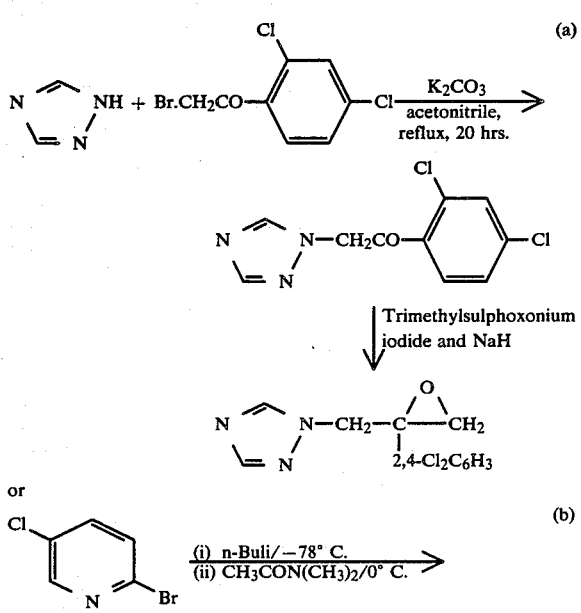

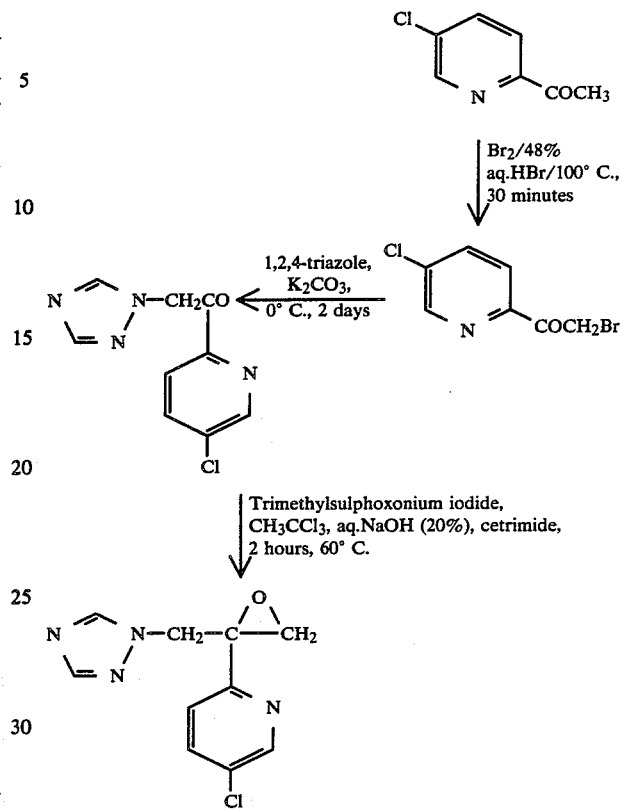

(9) 2-Methyl- or 2,2-dimethylnitriles of formula (XI) are prepared, for example, by the following general route

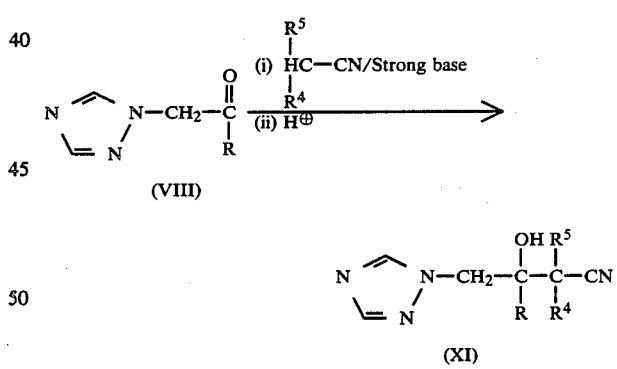

The preferred strong base is n-butyllithium. In a typical procedure, the nitrile is dissolved in a suitable solvent, e.g., dry tetrahydrofuran (THF), and the resulting solution is then cooled to about −70° C. A solution of n-butyllithium in hexane is then slowly added dropwise. After stirring for about one hour at −70° C., the ketone (VIII) in a suitable solvent, e.g., dry THF, is slowly added dropwise. After stirring for about an hour at −70° C. glacial acetic acid in a little THF is added and the reaction mixture is allowed to warm to 0° C. The product is then isolated and purified conventionally. When one of $R^4$ and $R^5$ is H and the other is $CH_3$, the product will exist in two diastereoisomeric forms and these are often separated by chromatography.

The starting ketones of the formula (VIII) are either known compounds or can be prepared by conventional methods.

The compounds of the invention contain a chiral center or centers and the invention includes both the resolved and unresolved forms.

Pharmaceutically acceptable acid addition salts of the compounds of the formula (I) are those formed from strong acids which form non-toxic acid addition salts, such as hydrochloric, hydrobromic, sulfuric, oxalic and methanesulfonic acids.

The salts are obtained by conventional procedures, e.g., by mixing solutions containing equimolar amounts of the free base and desired acid, and the required salt is collected by filtration, if insoluble, or by evaporation of the solvent.

Also included are the alkali metal salts, preparable conventionally.

The compounds of the formula (I) and their pharmaceutically acceptable salts are antifungal agents, useful in combating fungal infections in animals, including humans. For example, they are useful in treating topical fungal infections in man caused by, among other organisms, species of Candida, Trichophyton, Microsporum or Epidermophyton, or in mucosal infections caused by Candida albicans (e.g., thrush and vaginal candidiasis). They are also useful in the treatment of systemic fungal infections caused by, for example, Candida albicans, Cryptococcus neoformans, Aspergillus fumigatus, Coccidioides, Paracoccidioides, Histoplasma or Blastomyces.

The in vitro evaluation of the antifungal activity of the compounds is carried out, e.g., by determining the minimum inhibitory concentration (m.i.c.) which is the concentration of the test compound in a suitable medium at which growth of the particular microorganism fails to occur. In practice, a series of agar plates, each having the test compound incorporated at a particular concentration is inoculated with a standard culture of, for example, Candida albicans and each plate is then incubated for 48 hours at 37° C. The plates are then examined for the presence or absence of growth of the fungus and the appropriate m.i.c. value is noted. Other microorganisms used in such tests include, e.g., Cryptococcus neoformans, Aspergillus fumigatus, Trichophyton spp; Microsporum spp; Epidermophyton floccosum, Coccidioides immitis and Torulopsis glabrata.

The in vivo evaluation of the compounds is carried out, e.g., at a series of dose levels by intraperitoneal or intravenous injection or by oral administration, to mice which are inoculated with a strain of Candida albicans. Activity is based on the survival of a treated group of mice after the death of an untreated group of mice following 48 hours observation. The dose level at which the compound provides 50% protection ($PD_{50}$) against the lethal effect of the infection is noted.

The in vivo oral $PD_{50}$ values for selected compounds of the invention, obtained with mice inoculated with a lethal dose of Candida albicans by the method described above, are summarized in the table below.

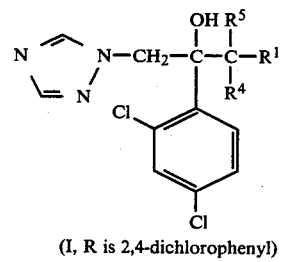

(I, R is 2,4-dichlorophenyl)

where $R^4$ and $R^5$ are each H and $R^1$ is as shown below.

| $R^1$ | Example No. | Oral $PD_{50}$ (mg/kg.) |
|---|---|---|
| $CONHCOCH_3$ | 22 | 0.1 |
| $CONHCOCH_2CH_3$ | 23 | 0.1 |
| CONHCO—⟨⟩—Cl | 24 | 0.1 |
| $CON(COOCH_3)_2$ | 25 | ca. 0.3 |

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral or parenteral administration to human patients, the daily dosage level of the antifungal compounds of the formula (I) will be from 0.1 to 5 mg/kg (in divided doses) when administered by either the oral or parenteral route. Thus tablets or capsules of the compounds will contain from 5 mg. to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) are administered in the form of a suppository or pessary, or they are applied topically in the form of a lotion, solution, cream, ointment or dusting powder. For example, they are incorporated into a cream consisting of an aqueous emulsion of polyethylene glycols or liquid paraffin; or incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rust, mildews and molds, and the compounds are thus useful for treating plants and seeds to eradicate or prevent such diseases.

The in vitro evaluation of the activity of the compounds against plant fungi is determined, e.g., by measuring their minimum inhibitory concentrations in the same way as previously described except that the plates are incubated at 30° C. for 48 hours or longer before being examined for the presence or absence of growth.

Microorganisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds are applied in the form of dusting powders, or granules, seed dressings, aqueous solutions, dispersions or emulsions, dips, sprays, aerosols or smokes. Compositions are also applied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example, they are applied directly to the plant foliage, stems, branches, seeds or roots or to the soil or other growing medium, and they can be used not only to eradicate disease, but also prophylactically to protect the plants or seeds from attack.

The following Examples illustrate the invention. All temperatures are in °C. Mixtures of solvents employed for chromatography are by volume.

EXAMPLE 1

1-Cyano-2-(2,4-dichlorophenyl)-3-(1H-1,2,4-triazol-1-yl)propan-2-ol

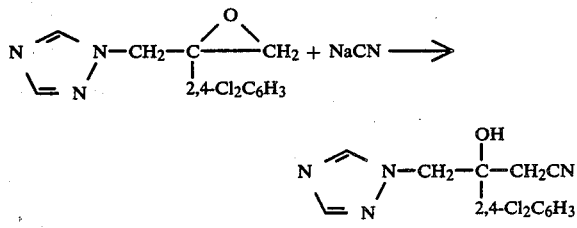

To 2-(2,4-Dichlorophenyl)-2-(1H-1,2,4-triazol-1-ylmethyl)oxirane (6.7 g) in dimethylformamide (198 ml) at 60° C. was added dropwise over 25 minutes, a solution of sodium cyanide (2.84 g) in water (49 ml). Heating at 60° C. was continued for five hours. The reaction mixture was then cooled, poured into water (900 ml), and extracted with ethyl acetate (3×150 ml). The combined organic extracts were washed with saturated aqueous brine, dried (Na2SO4) and evaporated to dryness to give a pale yellow solid (6.1 g) which was triturated with ethyl ether. The residual solid was recrystallized from ethyl ether/methanol to give the title compound, 4.13 g (56%), m.p. 217°–219° C.

Analysis %: Found: C, 48.3; H, 3.4; N, 18.4. Calculated for C12H10Cl2N4O: C, 48.5; H, 3.4; N, 18.8.

EXAMPLE 2

1-Cyano-2-(2,4-dichlorophenyl)-3-(1H-1,2,4-triazol-1-yl)propan-2-ol

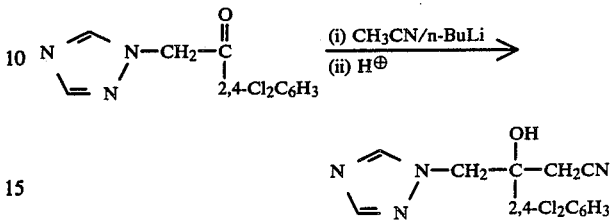

Acetonitrile (2.25 g, 0.055 mole) was dissolved in dry tetrahydrofuran (100 ml) and the resulting solution was cooled to −70° C. under nitrogen in a acetone/dry ice bath. A solution of n-butyllithium in hexane (39 ml, 1.55 molar, 0.060 mole) was added dropwise over five minutes. After stirring for about 45 minutes at −70° C., 2′,4′-dichloro-2-(1H-1,2,4-triazol-1-yl)acetophenone (12.8 g) in dry tetrahydrofuran (100 ml) was added dropwise over a 15 minute period. Stirring was continued at −70° C. for about one hour and then glacial acetic acid (20 ml) in tetrahydrofuran (20 ml) was added dropwise. The cooling bath was then removed. The reaction mixture was allowed to warm to 0° C., quenched in water (400 ml), and solid sodium carbonate was added to raise the pH to 8.0. After extraction with ethyl acetate (3×75 ml), the combined organic extracts were washed with saturated brine (3×50 ml), dried (Na2SO4) and evaporated to a pale yellow solid. This solid was washed well with ethyl ether to give the title compound (6.61 g, 44.5%), identical to the product of Example 1 as confirmed by n.m.r. and i.r. spectroscopy.

EXAMPLE 3

1-Cyano-2-(2,4-difluorophenyl)-3-(1H-1,2,4-triazol-1-yl)propan-2-ol was prepared similarly to the previous Example using 2′,4′-difluoro-2-(1H-1,2,4-triazol-1-yl)acetophenone as the starting ketone. It had an m.p. of 154°–155° C.

Analysis %: Found: C, 54.0; H, 3.8; N, 21.5. Calculated for C12H10F2N4O: C, 54.6; H, 3.8; N, 21.2.

EXAMPLE 4

1-Carbamoyl-2-(2,4-dichlorophenyl)-3-(1H-1,2,4-triazol-1-yl)propan-2-ol

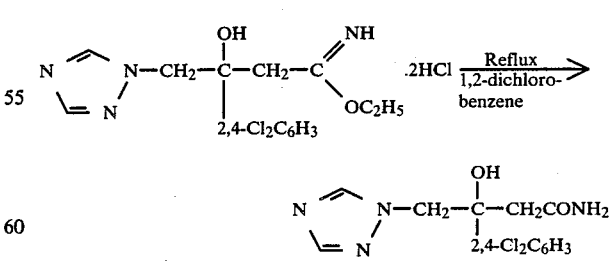

3-(2,4-Dichlorophenyl)-3-hydroxy-4-(1H-1,2,4-triazol-1-yl)butyrimidic acid, ethyl ester dihydrochloride (3.42 g) was suspended in 1,2-dichlorobenzene (35 ml) and the mixture was heated to the reflux temperature of the solvent (178° C.). After refluxing for five minutes, a solution was obtained. Refluxing was then continued for an additional 10 minutes. The reaction mixture was cooled, evaporated, and the resulting gum was triturated with hexane and heated with acetone. On cooling a cream colored granular solid was formed which was filtered to yield the title compound as a solvate (1.26 g). On standing overnight in a refrigerator some further solvated product precipitated (0.62 g). After drying at 80° C. for 6 hours to remove the solvent the pure (unsolvated) title compound was obtained, yield 1.5 g, m.p. 144°–145° C.

Analysis % (after said drying): Found: C, 45.5; H, 3.8; N, 17.5. Calculated for $C_{12}H_{12}Cl_2N_4O_2$: C, 45.7; H, 3.8; N, 17.8.

EXAMPLE 5

2-(2,4-Dichlorophenyl)-1-(N-methylcarbamoyl)-3-(1H-1,2,4-triazol-1-yl)propan-2-ol

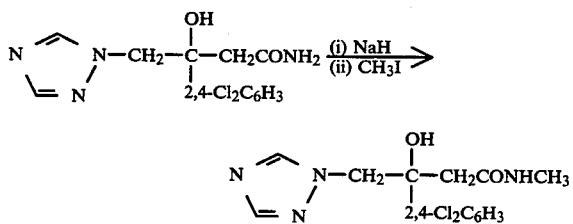

1-Carbamoyl-2-(2,4-dichlorophenyl)-3-(1H-1,2,4-triazol-1-yl)propan-2-ol (1.0 g) was dissolved in dry tetrahydrofuran (20 ml) and the reaction mixture was cooled to 0°–5° C. Sodium hydride (0.15 g, as a 50% dispersion in oil) was then added, the mixture stirred for 10 minutes and methyl iodide (0.45 g) added. Further quantities of methyl iodide (90 mg) and sodium hydride (375 mg, as a 50% dispersion in oil) were added. After stirring for a few minutes, yet further quantities of methyl iodide (90 mg) and sodium hydride (375 mg, as a 50% dispersion in oil) were added. The mixture was then quenched in water and extracted with ethyl acetate (3×50 ml). The combined organic extracts were dried (MgSO4) and evaporated to give the crude product as a gum. A solution of this gum in methylene chloride (20 ml) was chromatographed on a silica gel column (10 g), eluting with methylene chloride (100 ml), then with methylene chloride containing 2% isopropanol and 0.2% NH4OH (300 ml), and finally with methylene chloride containing 5% isopropanol and 0.5% NH4OH (500 ml). Appropriate fractions were collected to yield the title compound, which was recrystallized from cyclohexane (yield 41 mg, m.p. 151°–154° C.).

Analysis %: Found: C, 47.3; H, 4.35; N, 17.2. Calculated for $C_{13}H_{14}Cl_2N_4O_2$: C, 47.4; H, 4.3; N, 17.0.

EXAMPLE 6

2-(2,4-Dichlorophenyl)-1-(N-isopropylcarbamoyl)-3-(1H-1,2,4-triazol-1-yl)propan-2-ol 1-Carboxy-2-(2,4-dichlorophenyl)-3-(1H-1,2,4-triazol-1-yl)propan-2-ol 1-Cyano-2-(2,4-Dichlorophenyl)-3-(1H-1,2,4-triazol-1-yl)-2-propanol (4 g, 13.9 mmole) was dissolved in 40% aqueous sulfuric acid (100 ml) and heated in an oil bath at 100°–110° C. for 18 hours. The solution was then cooled, diluted with water (200 ml), and rendered alkaline by the slow addition of solid sodium bicarbonate. The mixture was then extracted several times with ethyl acetate (3×100 ml.) and the aqueous phase was rendered acidic (pH 3) by the addition of dilute orthophosphoric acid. The aqueous phase was then extracted with ethyl ether (3×150 ml), the combined ether extracts were washed once with water, and then dried over magnesium sulfate. Evaporation of the ether gave the title compound as a pale yellow solid, 2.7 g, (62%), m.p. 158°–159° C.

Analysis %: Found: C, 46.35; H, 3.5; N, 13.6. Required for $C_{12}H_{11}Cl_2N_3O_3$: C, 45.6; H, 3.5; N, 13.3.

(B)

N,N'-Dicyclohexylacarbodiimide ("DCCD") (110 mg, 0.5 mmole) dissolved in dry dioxan (5 ml) was added to a solution of 1-carboxy-2-(2,4-dichlorophenyl)-3-(1H-1,2,4-triazol-1-yl)propan-2-ol (150 mg, 0.5 mmole) and N-hydroxysuccinimide ("NHS") (60 mg, 0.5 mmole) in dry dioxan (10 ml), and the mixture was stirred at room temperature for 2 hours. The precipitate was filtered off, washed with dry dioxan (10 ml) and the combined filtrate and washings were then added to a solution of isopropylamine (200 mg, 3.4 mmole) in dry dioxan (2 ml). The resultant solution was left at room temperature for 18 hours, diluted with ethyl acetate (100 ml), washed three times with saturated brine solution and dried over magnesium sulfate. Evaporation of the filtrate gave an oil which was then chromatographed on "Kieselgel 60H" (Merck, Trade Mark) silica (10 g), eluting with methylene chloride containing 2% isopropyl alcohol and 0.2% aqueous ammonium hydroxide (Sp. gr. 0.880). The title compound was obtained after evaporation of appropriate fractions as a colorless solid, m.p. 105°–107° C.

Analysis %: Found: C, 50.7; H, 5.2; N, 15.3. Required for $C_{15}H_{18}N_4Cl_2O_2$: C, 50.6; H, 5.1; N, 15.7.

EXAMPLES 7–9

The following compounds were prepared similarly to the previous Example, starting from the same acid, DCCD/NHS and the appropriate amine:

| Example No. | R¹ | m.p. (°C.) | Analysis % Theoretical in Brackets | | |
|---|---|---|---|---|---|
| | | | C | H | N |
| 7 | —CONHC₂H₅ | 129–130° | 49.0 (49.0 | 4.8 4.7 | 15.8 16.3) |
| | | | (as hydrochloride) | | |
| 8 | —CONH(CH₂)₂CH₃ | 169–170° | 45.7 (45.8 | 4.8 4.9 | 14.0 14.2) |
| 9 | —CONHCH₂C(CH₃)₃ | 135–137° | 53.2 (53.0 | 5.9 5.8 | 14.7 14.5) |

EXAMPLE 10

The following compound was prepared by the procedure of Example 6, starting from 1-carboxy-2-(2,4-difluorophenyl)-3-(1H-1,2,4-triazol-1-yl)propan-2-ol, "DCCD", "NHS" and methylamine:

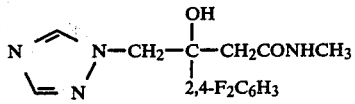

It melted at 129°–131° C.

Analysis %: Found: C, 52.8; H, 4.9; N, 19.3. Calculated for $C_{13}H_{14}F_2N_4O_2$: C, 52.7; H, 4.8; N, 18.9.

EXAMPLE 11

3-Cyano-2-(2,4-dichlorophenyl)-1-(1H-1,2,4-triazol-1-yl)butan-2-ol (2 diastereoisomeric forms)

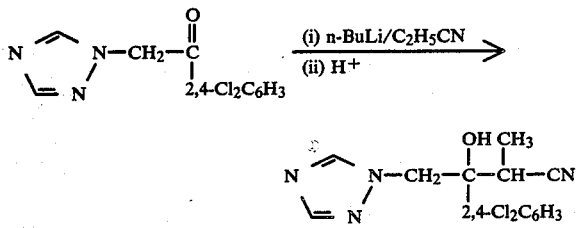

Propionitrile (1.21 g) in dry tetrahydrofuran (50 ml) was cooled to −72° C. A solution of n-butyllithium in n-hexane (14.2 ml, 1.55 molar) was then slowly added while maintaining the temperature of the reaction mixture at −45° C. or below. After stirring for about 30 minutes, 2-(1H-1,2,4-triazol-1-yl)-2',4'-dichloroacetophenone (2.56 g) in dry tetrahydrofuran (THF) (50 ml) was added slowly with stirring over a 20 minute period, the temperature of the mixing being maintained at −70° C. Stirring was continued at this temperature for one hour and then at −10° for a half hour, then glacial acetic acid (10 ml) in dry THF (15 ml) was added. The reaction mixture was allowed to warm to room temperature (20° C.), adjusted to pH 8 with solid sodium bicarbonate, and extracted with ethyl acetate (3×75 ml). The combined organic extracts were washed three times with water, dried (MgSO₄), evaporated and ethyl ether (30 ml) was added to the residue, yielding a white crystalline solid and a yellow solution. The solid was filtered off, dissolved in a small volume of methylene chloride, and loaded onto an 18 g. flash chromatography column of Merck's "Kieselgel 60" (Trade Mark) 230–400 mesh silica in ether (11×2 cm. diameter). Elution was carried out using 5% (by volume) acetone in ether at one p.s.i. (4.88 kg/m²). "Diastereoisomer 1" of the title compound was eluted first, 0.79 g, m.p. 178°–180° C.

Analysis %: Found: C, 50.0; H, 3.8; N, 17.9. Calculated for $C_{13}H_{12}Cl_2N_4O$: C, 50.2; H, 3.9; N, 18.0.

"Diastereoisomer 2" of the title compound was eluted next, 0.244 g, m.p. 202°–205° C.

Analysis %: Found: C, 50.4; H, 3.9; N, 17.6. Calculated for $C_{13}H_{12}Cl_2N_4O$: C, 50.2; H, 3.9; N; 18.0.

EXAMPLES 12 AND 13

The following compounds were prepared similarly to the previous Example, starting from the appropriate acetophenone, n-BuLi/C₂H₅CN and glacial acetic acid:

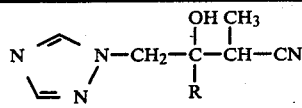

| Example No. | R | m.p. (°C.) | Analysis % Theoretical in Brackets | | |
|---|---|---|---|---|---|
| | | | C | H | N |
| 12 | ![4-Cl-phenyl] Cl (mixture of diastereomers, not separated) | 159–162° | 56.4 (56.4 | 4.8 4.7 | 20.0 20.2) |
| 13 | ![2,4-F2-phenyl] F F (believed to be a mixture diastereomers, not separated) | 185–187° | 56.2 (56.1 | 4.3 4.3 | 20.0 20.1) |

EXAMPLE 14

3-Carbamoyl-2-(2,4-dichlorophenyl)-1-(1H-1,2,4-triazol-1-yl)butan-2-ol hemihydrate and 3-carboxy-2-(2,4-dichlorophenyl)-1-(1H-1,2,4-triazol-1-yl)butan-2-ol 3-Cyano-2-(2,4-dichlorophenyl)-1-(1H-1,2,4-triazol-1-yl)butan-2-ol (700 mg, diastereoisomer 1 from the previous Example) was heated for 5½ hours at 90°–94° C. in 40% (by volume) aqueous sulfuric acid. The solution was then stirred at room temperature (20° C.) for 19 hours, after which time saturated aqueous sodium bicarbonate solution was added to raise the pH to 8.0. The solution was then extracted with ethyl acetate (3×50 ml). The combined organic extracts were washed with water, dried (MgSO₄) and evaporated to yield the 3-carbamoyl title compound, 105 mg, m.p. 215°–217° C. after trituration with ethyl ether.

Analysis % (3-carbamoyl compound) Found: C, 46.8; H, 4.5; N, 15.5. Calculated for $C_{13}H_{14}Cl_2N_4O_2.\frac{1}{2}H_2O$: C, 46.2; H, 4.5; N, 15.6.

The aqueous phases resulting from the ethyl acetate extractions were combined, acidified to pH 2.0 with dilute hydrochloric acid, and extracted with ethyl acetate (3×50 ml). The combined organic extracts were washed with water, dried (MgSO₄) and evaporated to yield the title acid. After trituration with ethyl ether, the pure acid, 485 mg, m.p. 236°–238° C., was obtained.

Analysis %: Found: C, 47.0; H, 3.9; N, 12.4. Calculated for $C_{13}H_{13}Cl_2N_3O_3$: C, 47.3; H, 4.0; N, 12.7.

EXAMPLE 15

3-Carbamoyl-2-(2,4-difluorophenyl)-1-(1H-1,2,4-triazol-1-yl)butan-2-ol ¼ hydrate, m.p. 170°–172° C., was prepared similarly to the previous Example by the hydrolysis of the corresponding nitrile prepared in Example 13 but using 80% (w/w) aqueous sulfuric acid.

Analysis %: Found: C, 52.0; H, 4.8; N, 18.5. Calculated for $C_{13}H_{14}F_2N_4O_2.\frac{1}{4}H_2O$: C, 51.9; H, 4.8; N, 18.6.

EXAMPLE 16

2-(4-Chlorophenyl)-3-carbamoyl-1-(1H-1,2,4-triazol-1-yl)butan-2-ol

The mixture of diastereomeric nitriles from Example 12 (3.9 g) was heated in sulfuric acid (80% by weight, 100 ml) for four hours at 60° C. The reaction mixture was then cooled, diluted with water (200 ml), and calcium carbonate (50 g) was added in small portions with external cooling (ice bath). The mixture was then filtered, and the material which had been filtered off was washed well with water (200 ml) and methanol (200 ml). The washings were added to the filtrate, evaporated to dryness, and the residue extracted with ethyl acetate (3×100 ml). The extracts were combined, dried (MgSO₄), and evaporated to a white solid, 2.73 g. This material was absorbed onto 7 g of silica gel by dissolution in the minimum quantity of a chloroform:methanol mixture (5:1, v/v), addition of the silica gel, and evaporation of the solvents. This silica gel was added as a suspension in ether to a silica gel column (25 g) and eluted with ether containing an increasing proportion of ethanol (2→10%). A proportion of the least polar amide diastereoisomer was eluted first in a pure state, and was recrystallized from ethyl acetate to give colorless crystals of one isomer of the title compound, m.p. 223°–225° C., 105 mg.

Analysis %: Found: C, 52.8; H, 5.3; N, 18.7. $C_{13}H_{15}ClN_4O_2$ requires: C, 53.0; H, 5.1; N, 19.0.

The remainder of the product was eluted as a mixture containing both the diastereoisomer characterized above and its more polar diastereomer (1:4 by NMR). Recrystallization from ethyl acetate gave colorless crystals, m.p. 186°–189° C., 404 mg.

Analysis %: Found: C, 53.0; H, 5.1; N, 19.4. $C_{13}H_{15}ClN_4O_2$ requires: C, 53.0; H, 5.1; N, 19.0.

EXAMPLE 17

2-(2,4-Dichlorophenyl)-3-(N-methyl-carbamoyl)-1-(1H-1,2,4-triazol-1-yl)butan-2-ol

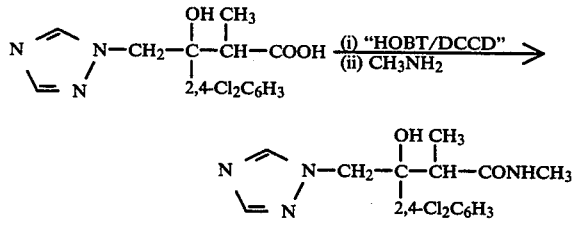

3-Carboxy-2-(2,4-dichlorophenyl)-1-(1H-1,2,4-triazol-1-yl)butan-2-ol (330 mg) was added to dry dioxan (10 ml) followed by 1-hydroxybenzotriazole hydrate ("HOBT") (203 mg) and dicyclohexylcarbodiimide ("DCCD") (618 mg). After stirring for 1 hour at room temperature (20° C.), methylamine (278 mg of 33% [by volume] solution in ethanol) was added and stirring was continued overnight (20 hours). The resulting precipitate of dicyclohexylurea was removed by filtration. The filtrate was added to water (50 ml) and solid sodium bicarbonate was added to pH 8.

The mixture was then extracted with ethyl acetate (3×50 ml) and the combined organic extracts were washed with water, dried (MgSO₄) and evaporated. The residue was dissolved in a small volume of methylene chloride and chromatographed on a Merck "Kieselgel 60" (Trade Mark) silica flash column in ethyl ether. Elution with ether (100 ml) followed by 15% (by volume) ethanol in ether (300 ml) yielded, by collection of appropriate fractions, the title compound, 29 mg. m.p. 242°–244° C.

Since the recovered dicyclohexylurea contained a further quantity of the title compound, this was dissolved in a small amount of methanol and absorbed onto Merck's "Kieselgel 60" (Trade Mark) silica (3 g), and the resulting slurry was then loaded onto a 10 g flash column of this material in ethyl ether. Elution with 10% (by volume) ethanol in ether, and collection of appropriate fractions followed by recrystallization from isopropanol, yielded a further quantity of the title compound (81 mg).

Analysis %: Found: C, 48.9; H, 4.8; N, 16.2. Calculated for $C_{14}H_{16}Cl_2N_4O_2$: C, 49.0; H, 4.7; N, 16.3.

EXAMPLE 18

(A)

2-(2,4-Dichlorophenyl)-3-ethoxycarbonyl-3-methyl-1-(1H-1,2,4-triazol-1-yl)butan-2-ol and 4-(2,4-dichlorophenyl)-3,3-dimethyl-4-(1H-1,2,4-triazol-1-ylmethyl)beta-propiolactone

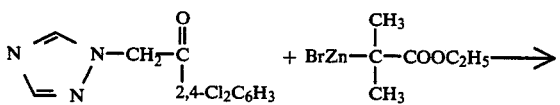

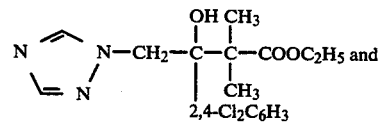

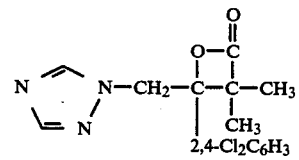

2-(1H-1,2,4-Triazol-1-yl)-2′,4′-dichloroacetophenone (2.56 g) in dry tetrahydrofuran (20 ml) and ethyl alpha-bromoisobutyrate (1.475 ml) in dry ether (10 ml) were added simultaneously to granulated zinc (1.5 g) in toluene (10 ml) over 20 minutes. The reaction mixture was then heated at 80° C. for 18 hours. The cooled reaction mixture was poured onto ice-cold sulfuric acid (0.2N, 125 ml) and extracted with ether (200 ml). The ether extract was washed with brine, dried (MgSO₄), and concentrated in vacuo. The residue was flash chromatographed on silica (120 g) and eluted with 80% ethyl acetate/20% hexane. The initial fractions yielded the title ester, which was crystallized from ethyl acetate/hexane, yield of the pure product, 61 mg, m.p. 95°–96° C.

Analysis %: Found: C, 51.7; H, 5.2; N, 11.1. Calculated for $C_{16}H_{19}Cl_2N_3O_3$: C, 51.6; H, 5.1; N, 11.3.

The later fractions on evaporation gave the title beta-lactone, which was recrystallized from ethyl acetate/hexane, yield of the pure product 240 mg, m.p. 177°–178° C.

Analysis %: Found: C, 51.8; H, 3.9; N, 12.8. Calculated for $C_{14}H_{13}Cl_2N_3O_2$: C, 51.5; H, 4.0; N, 12.9.

(B)
3-Carbamoyl-2-(2,4-dichlorophenyl)-3-methyl-1-(1H-1,2,4-triazol-1-yl)butan-2-ol To a solution of 2-(2,4-dichlorophenyl)-3-ethoxycarbonyl-3-methyl-1-(1H-1,2,4-triazol-1-yl)butan-2-ol (75 mg) in ethanol (5 ml), aqueous ammonia (sp. gr. 0.88, 12 ml.) was added and the solution was left at room temperature (20° C.) for eight days. The solvent was then evaporated in vacuo, the residue was partitioned between methylene chloride and water, and the organic extracts were washed with brine and dried (MgSO4). Removal of solvent followed by flash chromatography on silica (30 g) and elution with a mixture of methylene chloride/methanol/ammonia (93:7:1) gave the title compound, m.p. 162°–163° C. (34.5 mg).

Analysis %: Found: C, 48.8; H, 4.7; N, 15.8. Calculated for $C_{14}H_{16}Cl_2N_4O_2$: C, 49.0; H, 4.7; N, 16.3.

(C) 1-Carbamoyl-2-(2,4-dichlorophenyl)-3-(1H-1,2,4-triazol-1-yl)propan-2-ol was prepared similarly to parts (A) and (B) above from appropriate starting materials, and was confirmed spectroscopically to be identical to the product of Example 4.

(D)
3-Carbamoyl-2-(2,4-dichlorophenyl)-3-methyl-1-(1H-1,2,4-triazol-1-yl)butan-2-ol [alternative method to (B) above]

A solution of 4-(2,4-dichlorophenyl)-3,3-dimethyl-4-(1H-1,2,4-triazol-1-yl-methyl)-beta-propiolactone (70 mg) in ethanol (4 ml) was treated with 0.88 sp. gr. ammonia (6 ml) and left to stand at room temperature for five days. The reaction mixture was then evaporated in vacuo and extracted and chromatographed by the method described in part (B) above to yield the title compound, m.p. 162°–163° C., (41 mg).

Analysis %: Found: C, 48.6; H, 4.7; N, 15.9. Calculated for $C_{14}H_{16}Cl_2N_4O_2$: C, 49.0; H, 4.7; N, 16.3.

EXAMPLE 19

2-(2,4-Dichlorophenyl)-3-methyl-3-(N-methylcarbamoyl)-1-(1H-1,2,4-triazol-1-yl)butan-2-ol A solution of 4-(2,4-dichlorophenyl)-3,3-dimethyl-4-(1H-1,2,4-triazol-1-ylmethyl)-beta-propiolactone (200 mg) in ethanol (5 ml) was treated with a solution of 35% (by volume) methylamine in ethanol (5 ml), and the resulting solution was left to stand overnight at room temperature (20° C.). After evaporating residual methylamine and ethanol, the residue was triturated with hexane and the resulting solid was crystallized from ethyl acetate/hexane to yield the title compound, m.p. 145°–146° C., (120 mg).

Analysis %: Found: C, 50.2; H, 5.0; N, 15.9. Calculated for $C_{15}H_{18}Cl_2N_4O_2$: C, 50.4; H, 5.0; N, 15.7.

EXAMPLE 20

(A)
4-(2,4-Dichlorophenyl)-4-(1H-1,2,4-triazol-1-ylmethyl)-beta-propiolactone

3-Carboxy-2-(2,4-dichlorophenyl)-1-(1H-1,2,4-triazol-1-yl)propan-2-ol (948 mg) was dissolved in dry dioxan (20 ml) and 1-hydroxybenzotriazole hydrate (0.61 g) followed by dicyclohexylcarbodiimide (1.85 g), was then added. The resulting mixture was stirred at room temperature (20° C.) for two hours, triethylamine (455 mg) was added and stirring was continued overnight (19 hours). The mixture was added to water (100 ml) and extracted with ethyl acetate (3×50 ml). The precipitate of dicyclohexylurea was removed by filtration after the first extraction. The combined organic extracts were washed with water, dried (MgSO4) and evaporated. The residue was dissolved in a small amount of methylene chloride and loaded onto a flash column of Merck's "Kieselgel 60" (Trade Mark) silica (12 g, 230–400 mesh) in ethyl ether. Elution with ethyl ether (100 ml) and then with 5% (by volume) acetone in either (300 ml) gave, after collection of appropriate fractions, the title compound, 600 mg, m.p. 178°–180° C.

Analysis %: Found: C, 48.1; H, 3.0; N, 14.0. Calculated for $C_{12}H_9Cl_2N_3O_2$: C, 48.4; H, 3.0; N, 14.1.

(B)
1-(N-Methylcarbamoyl)-2-(2,4-dichlorophenyl)-3-(1H-1,2,4-triazol-1-yl)propan-2-ol

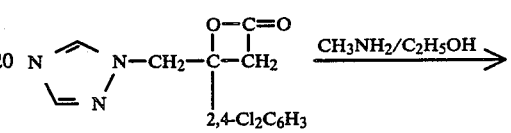

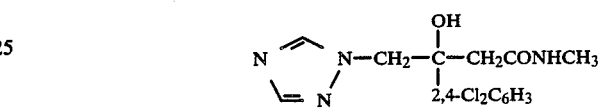

This reaction was carried out by the method of Example 19 using the starting materials specified in the reaction scheme to give the title compound, confirmed spectroscopically to be the desired product and to be identical to the product of Example 5.

EXAMPLE 21

1-Carbamoyl-2-(2,4-dichlorophenyl)-3-(1H-1,2,4-triazol-1-yl)propan-2-ol

This reaction was carried out by the method of Example 18(D) using the beta-propiolactone provided above to give the title compound, confirmed spectroscopically to be the desired product and to be identical to the product of Example 4.

EXAMPLE 22

3-(N-Acetylcarbamoyl)-2-(2,4-dichlorophenyl)-1-(1H-1,2,4-triazol-1-yl)propan-2-ol hemihydrate

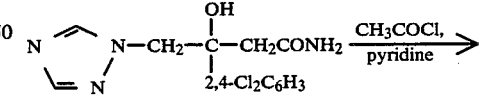

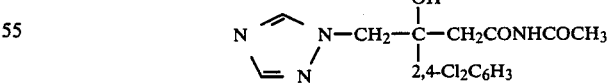

A solution of acetyl chloride (0.12 g, 1.5 mmole) in dry acetonitrile (2 ml) was added dropwise to a stirred solution of 3-carbamoyl-2-(2,4-dichlorophenyl)-1-(1H-1,2,4-triazol-1-yl)propan-2-ol (0.314 g., 1 mmole) and pyridine (0.12 g., 1.5 mmole) in dry acetonitrile (2 ml) at −20° C. The solution was allowed to warm to room temperature and was stirred at room temperature for a further 18 hours. The solvent was then removed under reduced pressure and the residue was partitioned between water (10 ml) and chloroform (40 ml). The organic phase was separated, dried over MgSO$_4$ and evaporated. The residue was chromatographed on silica eluting with 10:1 (v:v) chloroform/methanol and the fractions containing the product were combined, evaporated, and recrystallized from diisopropyl ether to furnish the title compound, (67 mg., 19%), m.p. 148°–150° C.

Analysis %: Found: C, 45.8; H, 3.9; N, 15.0. Calculated for C$_{14}$H$_{14}$N$_4$O$_3$Cl$_2$.1/2H$_2$O: C, 45.9; H, 4.1; N, 15.3.

EXAMPLES 23 AND 24

The following compounds were prepared similarly to Example 22, starting from the same amide, pyridine, and the appropriate acid chloride of the formula R$^3$.Cl:

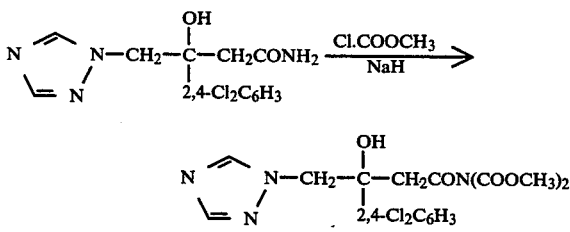

| Example No. | R$^3$ | m.p. (°C.) | Analysis % Theoretical in Brackets | | |
|---|---|---|---|---|---|
| | | | C | H | N |
| 23 | CH$_3$CH$_2$—C— ‖ O | 101–103° | 48.2 (48.5 | 4.3 4.3 | 14.7 15.1) |
| 24 | Cl—⟨⟩—C— ‖ O | 183–184° | 50.3 (50.3 | 3.4 3.3 | 12.1 12.3) |

EXAMPLE 25

2-(2,4-Dichlorophenyl)-3-(N,N-dimethoxycarbonylcarbamoyl)-1-(1H-1,2,4-triazol-1-yl)propan-2-ol 3-Carbamoyl-2-(2,4-dichlorophenyl)-1-(1H-1,2,4-triazol-1-yl)propan-2-ol (0.94 g., 3 mmole) was added to a suspension of oil-free sodium hydride (0.14 g., 5.8 mmole) in dry tetrahydrofuran (10 ml). The suspension was stirred for one hour and then a solution of methyl chloroformate (0.6 g., 6.3 mmole) in dry tetrahydrofuran (10 ml) was added dropwise over 15 minutes. The mixture was stirred at room temperature for three hours and then the solvent was evaporated in vacuo. The residue was partitioned between saturated aqueous sodium bicarbonate solution (10 ml) and ethyl acetate (40 ml), and the organic phase was separated, washed with brine (10 ml), dried (MgSO$_4$) and evaporated. The residue was chromatographed on silica eluting with ethyl acetate/methanol 95:5 (v:v), and the fractions containing the product were combined and evaporated and recrystallized from ethyl acetate-hexane to give the title compound, (62 mg, 5%), m.p. 155°–156° C.

Analysis %: Found: C, 44.5; H, 3.7; N, 13.2. Calculated for C$_{16}$H$_{16}$N$_4$O$_6$Cl$_2$: C, 44.5; H, 3.7; N, 13.0.

EXAMPLE 26

1-Carbamoyl-2-(2,4-dichlorophenyl)-3-1H-1,2,4-triazol-1-yl)propan-2-ol

Bis(trimethylsilyl)acetamide (BSA) (1.99 g) was stirred at −70° C. in dry tetrahydrofuran (15 ml) while n-butyllithium in hexane (6.3 ml, 1.55M) was added dropwise over ten minutes. The resulting solution was stirred at −70° C. for 30 minutes, then a solution of 2-(1H-1,2,4-triazol-1-yl)-2'-4'-dichloroacetophenone (1.0 g) in dry tetrahydrofuran (10 ml) was added dropwise over 10 minutes, and the mixture was allowed to warm to room temperature, and water (5 ml) and hydrochloric acid (7 ml, 2N) were added. The mixture was adjusted to pH 8 by the addition of solid sodium bicarbonate, and extracted with ethyl acetate (3×10 ml). The combined extracts were washed with saturated sodium chloride solution (3×10 ml), dried (MgSO$_4$), and evaporated to a gum, 1.1 g.

This gum was chromatographed on silica ("Kieselgel 60", Merck), eluting with ether containing 5% by volume ethanol. After the elution of unreacted ketone, the product was eluted. The product-containing fractions were combined and evaporated to give the pure title compound, (0.21 g), confirmed spectroscopically to be identical to the product of Example 4.

EXAMPLE 27

1-Carbamoyl-2-(2,4-dichlorophenyl)-3-(1H-1,2,4-triazol-1-yl)propan-2-ol by acid hydrolysis of nitrile 1-Cyano-2-(2,4-dichlorophenyl)-3-(1H-1,2,4-triazol-1-yl)propan-2-ol (1.0 g) was heated at 60° C. for 2½ hours in sulfuric acid (10 ml, 80% w/w). The mixture was cooled to room temperature, carefully treated with water (100 ml), and adjusted to pH 9 with solid sodium hydroxide. The resulting solution was extracted with methylene chloride (3×50 ml), and the combined extracts evaporated to a gum, which was chromatographed on silica gel, eluting with methylene chloride containing 3% by volume methanol, increasing to 6% methanol. The fractions which contained the product (as judged by thin-layer chromatography) were combined and evaporated to a white solid, 0.91 g. This was dissolved in a mixture of acetone and methylene chloride at reflux and the product was precipitated by the addition of hexane to give fine crystals, m.p. 144°–145.5° C., 0.61 g, confirmed spectroscopically to be indentical with the product of Example 4 after drying under vacuum for 7 hours at 80° C.

EXAMPLE 28

The following illustrate pharmaceutical compositions for the treatment of fungal infections:

(a) Capsule: 71 parts by weight of the compound of Example 22 or 23 or granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 24 are dissolved in 10 parts of propylene glycol and mixed into 88 parts of a vanishing cream base.

(c) Pessary: 2 parts by weight of the compound of Example 25 are suspended in 98 parts of a warm liquified suppository base which is poured into molds and allowed to solidify.

EXAMPLE 29

By employing the appropriate 2-R-subsitituted-2-(1H-1,2,4-triazol-1-ylmethyl)oxirane in the procedure of Example 1 or the appropriate ketone in the procedure of Example 2 the following nitriles are obtained.

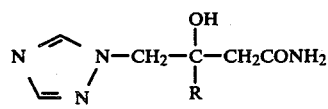

| R | R |
|---|---|
| 4-FC$_6$H$_4$ | 3-FC$_6$H$_4$ |
| 4-ClC$_6$H$_4$ | 3-IC$_6$H$_4$ |
| 4-BrC$_6$H$_4$ | 3-Br—5-IC$_6$H$_3$ |
| 4-IC$_6$H$_4$ | 2-Cl—4-CF$_3$C$_6$H$_3$ |
| 4-CF$_3$C$_6$H$_4$ | 2,4-(CF$_3$)$_2$C$_6$H$_3$ |
| 2-ClC$_6$H$_4$ | 2,4-Br$_2$C$_6$H$_3$ |
| 2-BrC$_6$H$_4$ | 2,5-Cl$_2$C$_6$H$_3$ |
| 2,5-F$_2$C$_6$H$_3$ | 5-chloro-2-pyridyl |
| 2-F—4-ClC$_6$H$_3$ | 4-CH$_3$C$_6$H$_4$ |
| 2-Cl—4-FC$_6$H$_3$ | 4-(CH$_3$)$_2$CHC$_6$H$_4$ |
| 2,4,6-F$_3$C$_6$H$_2$ | 4-(CH$_3$)$_3$CC$_6$H$_4$ |
| 4-Br—2,5-F$_2$C$_6$H$_2$ | 4-n-C$_4$H$_9$C$_6$H$_4$ |
| 2-Cl—4-CH$_3$C$_6$H$_3$ | 2-Cl—4-CH$_3$OC$_6$H$_3$ |
| 4-CH$_3$OC$_6$H$_4$ | 4-n-C$_4$H$_9$OC$_6$H$_4$ |
| 4-Cl—2-CH$_3$O—C$_6$H$_3$ | 2-Cl—4-n-C$_3$H$_7$OC$_6$H$_3$ |

EXAMPLE 30

The nitriles provided in the previous Example are converted to imido ether hydrochlorides by the method described in Preparation A and this intermediate is converted to an amide of the formula below by the method of Example 4.

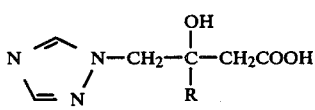

where R is as defined in the previous Example.

EXAMPLE 31

Employing the nitrile provided in Example 3 as starting material in the hydrolysis procedure of Example 6, Part A provided 1-carboxy-2-(2,4-difluorophenyl)-3-(1H-1,2,4-triazol-1-yl)propan-2-ol, m.p. 185°–187° C.

Analysis %: Found: C, 50.8; H, 3.9; N, 14.8. Calculated for C$_{12}$H$_{11}$F$_2$N$_3$O$_3$: C, 50,0; H, 3.9; N, 14.8.

The remaining nitriles provided in Example 29 are converted to the corresponding carboxylic acid of the formula below in like manner.

$$N\overset{\frown}{\underset{N}{\diagdown}}N-CH_2-\underset{\underset{R}{|}}{\overset{\overset{OH}{|}}{C}}-CH_2COOH$$

EXAMPLE 32

The above carboxylic acids are reacted with the appropriate amine of formula HNR$^2$R$^3$ by the procedure of Example 6, Part B to provide the amides of the formula below.

$$N\overset{\frown}{\underset{N}{\diagdown}}N-CH_2-\underset{\underset{R}{|}}{\overset{\overset{OH}{|}}{C}}-CH_2CONHR^2$$

| R | R$^2$ |
|---|---|
| 4-FC$_6$H$_4$ | H |
| 4-ClC$_6$H$_4$ | CH$_3$ |
| 4-BrC$_6$H$_4$ | H |
| 4-IC$_6$H$_4$ | C$_2$H$_5$ |
| 4-CF$_3$C$_6$H$_4$ | (CH$_2$)$_3$CH$_3$ |
| 2-ClC$_6$H$_4$ | H |
| 2-BrC$_6$H$_4$ | CH$_3$ |
| 2,5-F$_2$C$_6$H$_3$ | (CH$_2$)$_3$CH$_3$ |
| 2-F—4-ClC$_6$H$_3$ | H |
| 2-Cl—4-FC$_6$H$_3$ | CH$_3$ |
| 2,4,6-F$_3$C$_6$H$_2$ | CH$_3$ |
| 4-Br—2,5-F$_2$C$_6$H$_2$ | CH$_3$ |
| 2-Cl—4-CH$_3$C$_6$H$_3$ | H |
| 4-CH$_3$OC$_6$H$_4$ | C$_2$H$_5$ |
| 4-Cl—2-CH$_3$OC$_6$H$_3$ | H |
| 3-FC$_6$H$_4$ | H |
| 3-IC$_6$H$_4$ | H |
| 3-BrC$_6$H$_4$ | H |
| 3-Br—5-IC$_6$H$_3$ | C$_2$H$_5$ |
| 2-Cl—4-CF$_3$C$_6$H$_3$ | H |
| 2,4-(CF$_3$)$_2$C$_6$H$_6$ | H |
| 2,4-Br$_2$C$_6$H$_3$ | H |
| 2,4-Cl$_2$C$_6$H$_3$ | CH$_3$ |
| 2,4-Cl$_2$C$_6$H$_3$ | i-C$_3$H$_7$ |
| 2,5-Cl$_2$C$_6$H$_3$ | CH$_3$ |
| 5-chloro-2-pyridyl | H |
| 5-chloro-2-pyridyl | CH$_3$ |
| 5-chloro-2-pyridyl | C$_2$H$_5$ |
| 5-chloro-2-pyridyl | i-C$_3$H$_7$ |
| 5-chloro-2-pyridyl | sec-C$_4$H$_9$ |
| 4-CH$_3$C$_6$H$_4$ | CH$_3$ |
| 4-(CH$_3$)$_2$CHC$_6$H$_4$ | H |
| 4-(CH$_3$)$_3$CC$_6$H$_4$ | C$_2$H$_5$ |
| 4-n-C$_4$H$_9$C$_6$H$_4$ | CH$_3$ |
| 2-Cl—4-CH$_3$OC$_6$H$_3$ | H |
| 4-n-C$_4$H$_9$OC$_6$H$_4$ | H |
| 2-Cl—4-n-C$_3$H$_7$OC$_6$H$_3$ | CH$_3$ |
| C$_6$H$_5$ | CH$_3$ |

EXAMPLE 33

Employing an amide selected from those provided in Examples 10, 14–19 and 32 as starting materials in the procedure of Example 22 and the appropriate acid chloride, acid bromide or acid anhydride selected from acetyl bromide, propionyl chloride, n-butyryl chloride, isobutyric anhydride, propionic anhydride, benzoyl chloride, 2,4-dichlorobenzoyl bromide, 3-fluorobenzoyl chloride, 2-bromobenzoyl bromide, 4-iodobenzoyl chloride, 4-CF$_3$C$_6$H$_4$COCl, 3-CH$_3$C$_6$H$_4$COCl, 4-(CH$_3$)$_2$CHC$_6$H$_4$COCl, 2-CH$_3$OC$_6$H$_4$COCl, 4-t-C$_4$H$_9$C$_6$H$_4$COCl, 4-n-C$_4$H$_9$OC$_6$H$_4$COCl or 3,5-F$_2$C$_6$H$_3$COCl, as acylating agent affords the corresponding compounds of the formula below where R, R$^2$, R$^4$ and R$^5$ are as defined for the starting amide and R$^3$ is acetyl, propionyl, isobutyryl, n-butyryl, or one of the benzoyl groups derived from the above benzoyl chlorides.

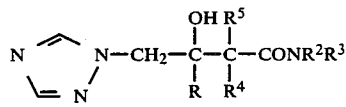

EXAMPLE 34

Similarly by employing one of the primary amides provided above as a starting material in the procedure of Example 25 and the appropriate alkyl haloformate of formula $$\underset{\text{XCO(C}_1\text{-C}_4 \text{ alkyl)}}{\overset{\text{O}}{\|}}$$

where X is Cl or Br as a reactant, provides the corresponding N,N-dialkoxycarbonyl amides of the formula

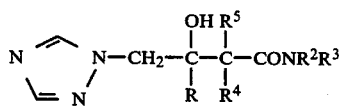

where R, $R^4$ and $R^5$ are as defined for the starting amide and $R^2$ and $R^3$ are the same and are methoxycarbonyl, ethoxycarbonyl, n-propoxycarbonyl, isopropoxycarbonyl, n-butoxycarbonyl, sec-butoxycarbonyl or t-butoxycarbonyl.

PREPARATION A 3-(2,4-Dichlorophenyl)-3-hydroxy-4-(1H,1,2,4-triazol-1-yl)butyrimidic acid, ethyl ester dihydrochloride 1-Cyano-2-(2,4-dichlorophenyl)-3-(1H,-1,2,4-triazol-1-yl)propan-2-ol (1 g) was dissolved in dry ethyl alcohol (100 ml) and dry halogen chloride gas was bubbled in, at 0° C., for 10 minutes. The reaction mixture was then stirred at room temperature overnight, and then the solvent was decanted from the solid. The solid was then washed with dry ether and dried to yield the title compound, (1.15 g), m.p. 154°–156° C. The product was used in Example 4.

Analysis %: Found: C, 40.6; H, 4.4; N, 13.6. Calculated for $C_{14}H_{16}Cl_2N_4O_2 \cdot 2HCl$: C, 40.4; H, 4.4; N, 13.5.

PREPARATION B (i) 2-(1H-1,2,4-Triazol-1-yl)-2',4'-dichloro acetophenone (Y)

This compound was prepared similarly to the method described in British Patent Specification No. 1512918:

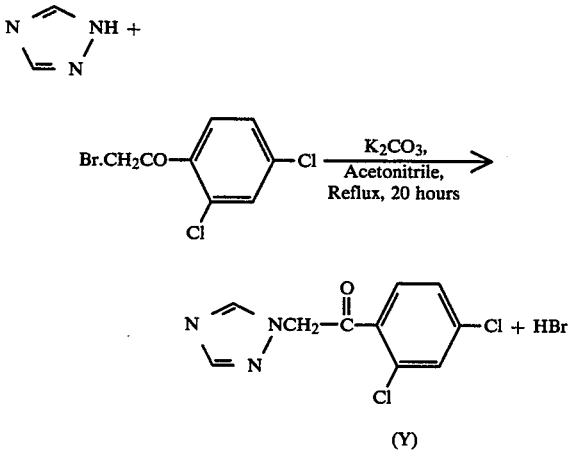

(ii) 2-(2,4-Dichlorophenyl)-2-(1H-1,2,4-triazol-1-ylmethyl)oxirane (Z)

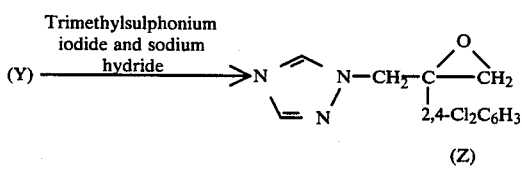

In 20 ml of dry ethyl ether, 3.78 g (0.079 mole) of sodium hydride (50% dispersion in oil) was suspended with stirring. The ether was then removed by decantation, and the sodium hydride was dried in a stream of dry nitrogen. Dry dimethyl sulphoxide (100 ml) was added followed by 17.34 g (0.079 mole) of dry powdered trimethylsulphonium iodide, in portions, over 15 minutes. The resulting mixture was stirred for 30 minutes at room temperature 20° C.). 18.33 g (0.072 mole) of compound (Y) as a solution in 50 ml of dry dimethyl sulphoxide was then added. The mixture was heated at 60° C. for three hours and then stood at room temperature overnight. The reaction mixture was cooled and quenched in ice. The product was then extracted with ethyl acetate (600 ml). The ethyl acetate layer was separated, dried over magnesium sulphate, and concentrated to give a red gum. Column chromatography of the gum on silica, eluting with ethyl ether, gave the product (Z). On evaporation, 6.62 g (34.4%) of the title product (Z) was obtained as a gum which solidified on trituration. The pure product melted at 57°–59° C.

Analysis %: Found: C, 48.6; H, 3.3; N, 15.3. Calculated for $C_{11}H_9Cl_2N_3O$: C, 49.0; H, 3.4; N, 15.5.

PREPARATION C (i) Preparation of 2-chloro-2',4'-difluoroacetophenone

Chloroacetyl chloride (113 g, 1.0 mole) was added dropwise to a stirred mixture of 1,3-difluorobenzene (114 g, 1.0 mole) and anhydrous aluminum chloride (146.6 g, 1.1 mole) at room temperature (20° C.). The mixture was stirred for a further five hours at 50°–55° C. Methylene chloride (48.5 ml) was added slowly as the mixture was allowed to cool to room temperature. The methylene chloride layer was separated, washed with water (2×320 ml) and the solvent removed by distillation at reduced pressure leaving a pale yellow solid (180 g).

A portion of the crude product (145 g) was crystallized from n-hexane (435 ml) giving the title compound (113 g, 73%) m.p. 47°–49° C. (literature* 46.5° C.) IR (KBr) and NMR (CDCl₃) were consistent with the desired structure.

*Von. D. Ehlers, et al., J. Prakt. Chem., 315, 1169 (1973).

(ii) 2',4'-Difluoro-2-(1H-1,2,4-triazol-1-yl)acetophenone hydrochloride

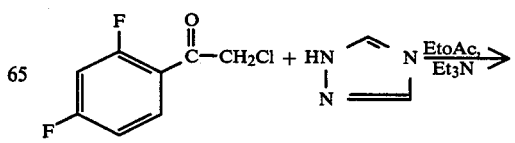

-continued

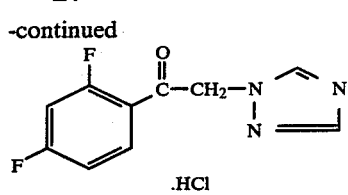
.HCl

To a mixture of 1,2,4-triazole (30.4 g, 0.44 mole) and triethylamine (15.1 g, 0.15 mole) in refluxing ethyl acetate (186 ml) was added a solution of 2-chloro-2',4'-difluoroacetophenone (38.1 g, 0.2 mole) in ethyl acetate (80 ml). The mixture was refluxed for six hours then cooled to room temperature and the insolubles were removed by filtration. The filtrate was washed with water (2×200 ml) and then the solvent was removed by distillation at reduced pressure. The crude product was dissolved in ethyl acetate (150 ml) then 25% w/v HCl gas in isopropanol was added. The mixture was granulated at 0° C. for one hour and then the solid was collected by filtration and dried to give the title compound (21.6 g, 40%), melting point 167°–170° C. IR (KBr) and NMR (DMSO) were consistent with the desired structure.

This intermediate was characterized as the free base, which was prepared by the following technique:

To a stirred slurry of sodium bicarbonate (16.8 g, 0.2 mole) and 1,2,4-triazole (27.6 g, 0.4 mole) in refluxing toluene (180 ml) was added to a solution of 2-chloro-2',4'-difluoroacetophenone (38.1 g, 0.2 mole) in toluene (45 ml). The mixture was stirred at reflux for three hours and the water formed during the reaction was removed using a Dean and Stark trap. The reaction mixture was cooled to room temperature and then water (180 ml) was added. The toluene layer was separated and the solvent removed by distillation at reduced pressure. The resulting pale brown solid was crystallized from 1:1 ethyl acetate:n-hexane (70 ml) give the title compound (3.9 g), melting point 103°–105° C. The IR (KBr) and NMR (CDCl$_3$) were consistent with the desired structure.

Analysis %: Found: C, 53.6; H, 3.15; N, 18.7 Calculated for C$_{10}$H$_7$F$_2$N$_3$O: C, 53.8; H, 3.2; N, 18.8.

For 4'-chloro-2-(1H-1,2,4-triazol-1-yl)acetophenone see German Patent Application No. 2,431,407.

We claim:

1. Compounds of the formula

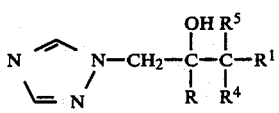 (I)

where R is phenyl optionally substituted by 1 to 3 substituents each independently selected from F, Cl, Br, I, CF$_3$, C$_1$–C$_4$ alkyl and C$_1$–C$_4$ alkoxy, or R is a 5-chloropyrid-2-yl group; R$^1$ is —CONR$^2$R$^3$ where either (a) R$^2$ is H or C$_1$–C$_4$ alkyl and R$^3$ is C$_2$–C$_4$ alkanoyl or benzoyl, said benzoyl group being optionally substituted by one or two substituents each independently selected from F, Cl, Br, I, CF$_3$, C$_1$–C$_4$ alkyl and C$_1$–C$_4$alkoxy; or (b) R$^2$ and R$^3$ are both (C$_1$–C$_4$ alkoxy)carbonyl;
R$^4$ and R$^5$ are each H or CH$_3$;
and their agriculturally or pharmaceutically acceptable acid addition salts.

2. A compound as claimed in claim 1 wherein R is phenyl substituted by one to three substituents each independently selected from F, Cl, Br, I and CF$_3$.

3. A compound as claimed in claim 2, wherein R is 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2,5-difluorophenyl, 2-fluoro-4-chlorophenyl, 2-chloro-4-fluorophenyl, 2,4,6-trifluorophenyl and 4-bromo-2,5-difluorophenyl.

4. A compound as claimed in claim 3, wherein R is 2,4-dichlorophenyl, 2,4-difluorophenyl or 4-chlorophenyl.

5. A compound as claimed in claim 4, wherein R is 2,4-dichlorophenyl.

6. A compound as claimed in claim 1 of the formula

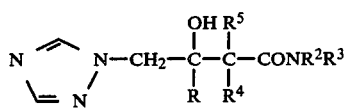

wherein R, R$^4$ and R$^5$ are as previously defined and either (a) R$^2$ is H and R$^3$ is acetyl, propionyl or p-chlorobenzoyl; or (b) R$^2$ or R$^3$ are both —COOCH$_3$.

7. A compound as claimed in claim 6 wherein R$^4$ and R$^5$ are each H.

8. A compound as claimed in claim 7 wherein R is 2,4-dichlorophenyl.

9. The compound as claimed in claim 8 wherein R$^2$ is H and R$^3$ is acetyl.

10. The compound as claimed in claim 8 wherein R$^2$ is H and R$^3$ is propionyl.

11. The compound according to claim 8 wherein R$^2$ is H and R$^3$ is p-chlorobenzoyl.

12. The compound according to claim 8 wherein R$^2$ and R$^3$ are both —COOCH$_3$.

13. A pharmaceutical composition comprising an antifungal amount of a compound or pharmaceutically acceptable salt according to claim 1 and a pharmaceutically acceptable diluent or carrier.

14. An agricultural antifungal composition suitable for use on a plant or seed which comprises an antifungal amount of a compound or agriculturally acceptable salt according to claim 1 and an agriculturally acceptable diluent or carrier.

15. A method of treating a fungal infection in an animal in need of such treatment which comprises administration to said animal an antifungal amount of a compound or pharmaceutically acceptable salt according to claim 1.

16. A method of treating a fungal infection in a plant or seed in need of such treatment which comprises administration to said plant or seed an antifungal amount of a compound or agriculturally acceptable salt according to claim 1.

* * * * *